US00PP18969P2

(12) United States Plant Patent
de Boer

(10) Patent No.: US PP18,969 P2
(45) Date of Patent: Jun. 24, 2008

(54) *ERYNGIUM* PLANT NAMED 'AMAZING JACKPOT'

(50) Latin Name: *Eryngium planum*
Varietal Denomination: Amazing Jackpot

(76) Inventor: Huibert Anne de Boer, Collegiantenstraat 90, 2231 HM Rijnsburg (NL)

( * ) Notice: Subject to any disclaimer, the term of this patent is extended or adjusted under 35 U.S.C. 154(b) by 0 days.

(21) Appl. No.: 11/725,807

(22) Filed: Mar. 20, 2007

(51) Int. Cl.
*A01H 5/00* (2006.01)

(52) U.S. Cl. ..... Plt./361

(58) Field of Classification Search ..... Plt./361
See application file for complete search history.

(56) References Cited

PUBLICATIONS

Upov CDROM search for cultivar Amazing Jackpot PBR 20042360.*

* cited by examiner

*Primary Examiner*—Annette H Para
(74) *Attorney, Agent, or Firm*—C. A. Whealy

(57) ABSTRACT

A new and distinct cultivar of *Eryngium* plant named 'Amazing Jackpot', characterized by its upright and inverted narrow triangular plant habit; moderately vigorous growth habit; freely branching habit; and broadly branched flower heads with dark blue-colored flowers.

2 Drawing Sheets

Botanical designation: *Eryngium planum.*
Cultivar denomination: 'Amazing Jackpot'

BACKGROUND OF THE INVENTION

The present invention relates to a new and distinct cultivar of *Eryngium* plant, botanically known as *Eryngium planum,* and hereinafter referred to by the name 'Amazing Jackpot'.

The new *Eryngium* originated from a cross-pollination in Rijnsburg, The Netherlands in July, 2000 made by the Inventor of a unnamed seedling selection of *Eryngium planum,* not patented, as the female, or seed, parent with the *Eryngium planum* cultivar Blue Candle, not patented, as the male, or pollen, parent. The new *Eryngium* was discovered and selected by the Inventor as a single flowering plant from within the progeny of the stated cross-pollination grown in a controlled environment in Rijnsburg, The Netherlands in July, 2001.

Asexual reproduction of the new *Eryngium* by cuttings in a controlled environment in Rijnsburg, The Netherlands since March, 2002, has shown that the unique features of this new *Eryngium* are stable and reproduced true to type in successive generations.

SUMMARY OF THE INVENTION

The cultivar Amazing Jackpot has not been observed under all possible environmental conditions. The phenotype may vary somewhat with variations in environment such as temperature and light intensity, without, however, any variance in genotype.

The following traits have been repeatedly observed and are determined to be the unique characteristics of 'Amazing Jackpot'. These characteristics in combination distinguish 'Amazing Jackpot' as a new and distinct cultivar of *Eryngium:*

1. Upright and inverted narrow triangular plant habit.
2. Moderately vigorous growth habit.

3. Freely branching habit.
4. Broadly-branched flower heads with dark blue-colored flowers.

Plants of the new *Eryngium* differ from plants of the female parent selection primarily in inflorescence form as plants of the parent selection have non-branching inflorescence heads.

Plants of the new *Eryngium* differ from plants of the male parent, the cultivar Blue Candle, in the following characteristics:

1. Plants of the new *Eryngium* and the cultivar Blue Candle differ in inflorescence form as plants of the cultivar Blue Candle have non-branching inflorescence heads.
2. Plants of the new *Eryngium* are not fragrant, whereas plants of the cultivar Blue Candle have an unpleasant fragrance.
3. Flowers of plants of the new *Eryngium* are sterile whereas flowers of plants of the cultivar Blue Candle are fertile.

Plants of the new *Eryngium* can also be compared to plants of the *Eryngium planum* cultivar Blue Ribbon, disclosed in U.S. Plant Pat. No. 7,151. Plants of the new *Eryngium* differ from plants of the cultivar Blue Ribbon primarily in inflorescence form and flower color.

BRIEF DESCRIPTION OF THE PHOTOGRAPHS

The accompanying photographs illustrate the overall appearance of the new *Eryngium.* The photographs show the colors as true as it is reasonably possible to obtain in colored reproductions of this type. Colors in the photographs may differ slightly from the color values cited in the detailed botanical description which accurately describe the colors of the new *Eryngium.*

The photograph on the first sheet comprises a side perspective view of a typical flowering stem of 'Amazing Jackpot'.

The photograph at the top of the second sheet is a close-up view of typical flowering stems of 'Amazing Jackpot'.

The photograph at the bottom of the second sheet is a close-up view of a typical inflorescences of 'Amazing Jackpot'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Rijnsburg, The Netherlands during the late summer in an outdoor nursery and under conditions and practices which approximate those generally used in commercial *Eryngium* production. During the production of the plants, day temperatures ranged from 15° C. to 22° C. and night temperatures ranged from 6° C. to 13° C. Measurements and numerical values represent averages for typical flowering plants. Plants were about one year old when the photographs and description were taken.

Botanical classification: *Eryngium planum* cultivar Amazing Jackpot.

Parentage:

*Female, or seed, parent.*—Unnamed seedling selection of *Eryngium planum,* not patented.

*Male, or pollen, parent.*—*Eryngium planum* cultivar Blue Candle, not patented.

Propagation:

*Type.*—By cuttings.

*Time to initiate roots.*—About 80 days at 12° C.

*Time to produce a rooted young plant.*—About six months at 18° C.

*Root description.*—Fibrous, fleshy and thick; white in color.

*Rooting habit.*—Freely branching; dense.

Plant description:

*Plant form/growth habit.*—Herbaceous perennial; upright and inverted narrow triangular plant habit; freely branching with about seven lateral branches developing per plant. Moderately vigorous growth habit.

*Plant height.*—About 61 cm.

*Plant diameter or spread.*—About 27 cm.

*Lateral branches.*—Length: About 7.7 cm. Diameter: About 2.5 mm. Aspect: Mostly upright to slightly outward. Strength: Strong. Texture: Smooth, glabrous. Color: Between 91A and 92A; towards the base, 145D.

Foliage description:

*Arrangement.*—Alternate, simple; sessile.

*Length, upper leaves.*—About 3.3 cm.

*Length, lower leaves.*—About 6.2 cm.

*Width, upper leaves.*—About 3.2 cm.

*Width, lower leaves.*—About 3.9 cm.

*Shape, upper leaves.*—Palmately lobed.

*Shape, lower leaves.*—Obovate.

*Apex, upper and lower leaves.*—Mucronulate.

*Base, upper leaves.*—Hastate.

*Base, lower leaves.*—Cordate.

*Margin, upper leaves.*—Serrate.

*Margin, lower leaves.*—Crenate.

*Texture, upper and lower leaves, upper and lower surfaces.*—Smooth, glabrous; leathery.

*Venation pattern, upper and lower leaves.*—Pinnate.

*Color, upper and lower leaves.*—Developing foliage, upper surface: Between 137C and 138A. Developing foliage, lower surface: 137D. Fully expanded foliage, upper surface: 138A; venation, 138A. Fully expanded foliage, lower surface: 146B to 146C; venation, 137C.

Flower description:

*Flower arrangement and habit.*—Single rotate flowers arranged on broadly branched flower heads; flowers sessile. Inflorescences arising from leaf axils. Freely flowering habit with usually about 400 flowers developing per inflorescence. Flowers persistent. Flowers face upright and outwardly. Flowers not fragrant.

*Natural flowering season.*—Plants of the new *Eryngium* initiate and develop flowers during the late summer and flower continuously from August through October in The Netherlands.

*Flowering longevity.*—Flowers last about two weeks on the plant.

*Inflorescence height.*—About 9.2 cm.

*Inflorescence diameter.*—About 6 cm.

*Flower diameter.*—About 2 mm.

*Flower length (depth).*—About 5 mm.

*Flower bud.*—Shape: Obovate. Length: About 1.5 mm. Diameter: About 1 mm. Color: 145B.

*Petals.*—Arrangement: Five petals in a single whorl. Length: About 2 mm. Width: About 1 mm. Shape: Elliptic. Apex: Acute; recurved. Margin: Entire. Texture, upper and lower surfaces: Smooth, glabrous. Color: When opening, upper and lower surfaces: 145D. Fully opened, upper and lower surfaces: 91A; towards the base, 145B; color becoming closer to 93B with development.

*Sepals.*—Arrangement: Five sepals in a single whorl. Length: About 2 mm. Width: About 1 mm. Shape: Ovate. Apex: Acute. Base: Cuneate. Margin: Entire. Texture, upper and lower surfaces: Smooth, glabrous. Color, immature, upper and lower surfaces: 137C; towards the base, 144C to 144D. Color, mature, upper surface: 137C; towards the base, 144C to 144D. Color, mature, lower surface: 137B.

*Inflorescence bracts.*—Arrangement: About 13 bracts in a single whorl subtending the flower head. Length: About 1.4 cm. Width: About 3 mm. Shape: Narrowly oblanceolate. Apex: Apiculate. Base: Cuneate. Margin: Entire. Texture, upper and lower surfaces: Smooth, glabrous. Color, immature and mature, upper surface: 137A; tinged with 91C. Color, immature and mature, lower surface: 137A.

*Peduncles.*—Length: About 3.9 cm. Diameter: About 2 mm. Angle: Main peduncle, about 10° from vertical; lateral peduncles, about 30° from vertical. Strength: Strong. Texture: Smooth, glabrous. Color: Between 91A and 92A.

*Reproductive organs.*—Stamens: Quantity/arrangement: About four per flower. Anther shape: Ovate. Anther length: About 1 mm. Anther color: 161D. Filament length: About 2.5 mm. Filament color: 91A. Pollen amount: Scarce. Pollen color: 156D. Pistils: Quantity: About three per flower. Pistil length: About 3 mm. Style length: About 2.8 mm. Style color: 91D; towards the base, 91B. Stigma shape: Rounded. Stigma color: 91D. Ovary color: 144B to 144C. Fruits/seeds: Fruit and seed development have not been observed.

Disease/pest resistance: Plants of the new *Eryngium* have not been shown to be resistant to pathogens and pests common to *Eryngium.*

Garden performance: Plants of the new *Eryngium* have exhibited good tolerance to rain and wind, have been observed to tolerate temperatures from about −20° C. to about 35° C.

It is claimed:

1. A new and distinct *Eryngium* plant named 'Amazing Jackpot' as illustrated and described.

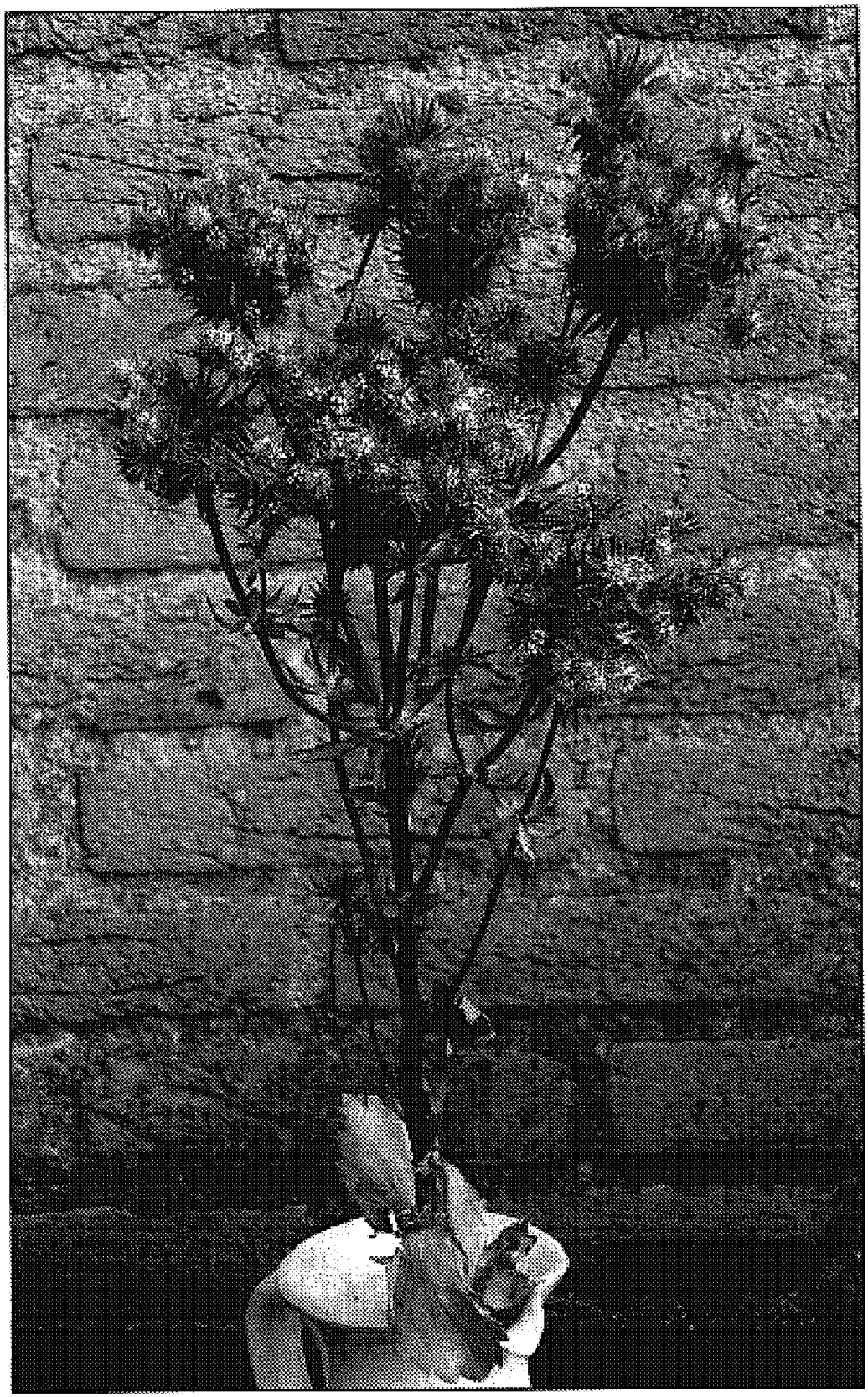

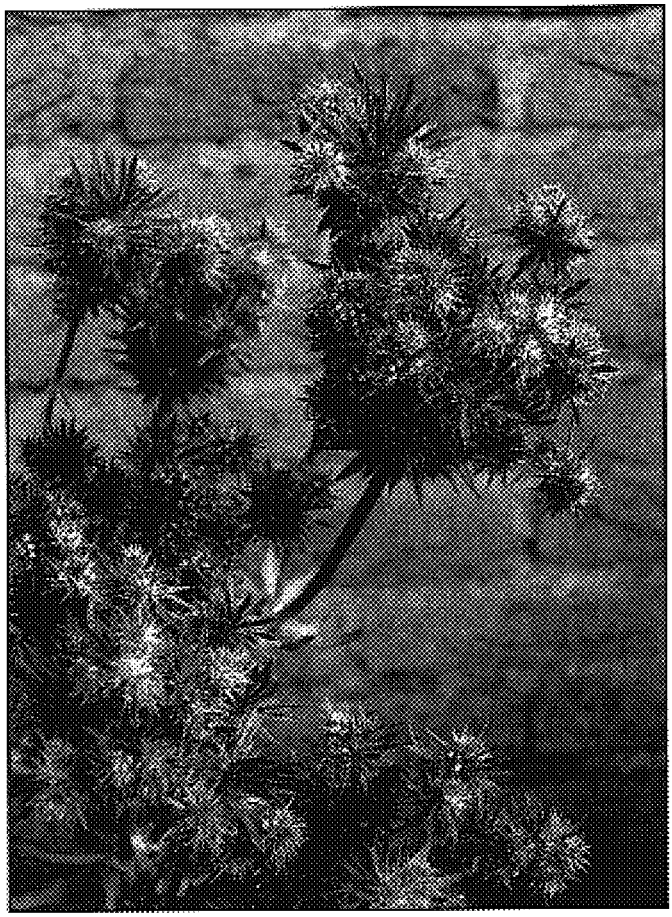
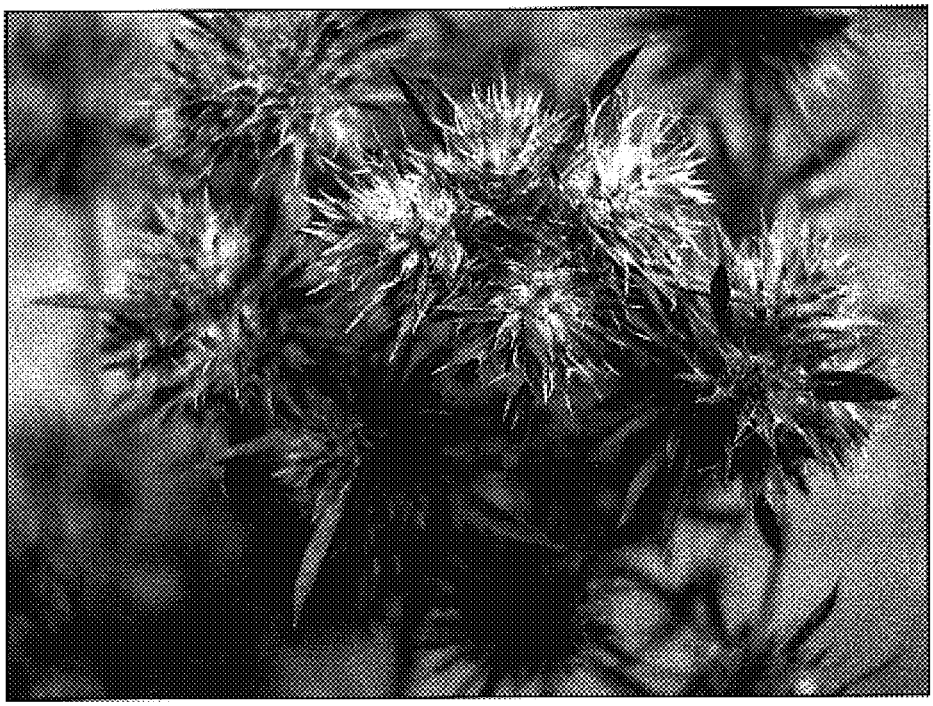

* * * * *